US006546281B1

(12) United States Patent
Zhang et al.

(10) Patent No.: US 6,546,281 B1
(45) Date of Patent: *Apr. 8, 2003

(54) INTEGRATED APPARATUS FOR CONTROLLED HEAT AIDED DERMAL DRUG DELIVERY

(75) Inventors: Jie Zhang, Salt Lake City, UT (US); Hao Zhang, Midvale, UT (US); Wade A. Hull, Taylorsville, UT (US); Larry Rigby, Salt Lake City, UT (US)

(73) Assignee: Zars, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/317,372

(22) Filed: May 24, 1999

Related U.S. Application Data

(62) Division of application No. 09/162,890, filed on Sep. 29, 1998, now Pat. No. 6,245,347, which is a continuation-in-part of application No. 08/819,880, filed on Mar. 18, 1997, now Pat. No. 5,919,479, which is a division of application No. 08/508,463, filed on Jul. 28, 1995, now Pat. No. 5,658,583.

(51) Int. Cl.[7] ............................................. A61N 1/30
(52) U.S. Cl. ...................... 604/20; 604/291; 604/113
(58) Field of Search ................. 604/20, 289–291, 604/304, 305, 306, 113, 114; 128/114.1; 607/96, 108; 424/443, 447–449

(56) References Cited

U.S. PATENT DOCUMENTS

| | | | | |
|---|---|---|---|---|
| 619,564 A | * | 2/1899 | Grimball | 604/291 |
| 1,433,304 A | * | 10/1922 | Sampson | 604/291 |
| 1,754,763 A | * | 4/1930 | Nunnally | 604/291 |
| 2,573,791 A | * | 11/1951 | Howells | 604/291 |
| 3,867,939 A | * | 2/1975 | Moore et al. | 128/254 |
| 3,929,131 A | | 12/1975 | Hardwick | 128/254 |
| 4,210,670 A | | 7/1980 | Cooke | 424/324 |
| 4,230,105 A | | 10/1980 | Harwood | 128/156 |
| 4,286,592 A | | 9/1981 | Chandrasekaran | 128/260 |
| 4,382,441 A | * | 5/1983 | Svedman | 604/291 |

(List continued on next page.)

FOREIGN PATENT DOCUMENTS

| | | |
|---|---|---|
| GB | 2 163 956 A | 12/1988 |
| WO | 8809169 | 1/1988 |
| WO | WO 97/01310 | 1/1997 |
| WO | WO 97/01311 | 1/1997 |
| WO | WO 97/01312 | 1/1997 |
| WO | WO 97/01313 | 1/1997 |
| WO | WO 97/36968 | 10/1997 |
| WO | WO 97/49361 | 12/1997 |
| WO | WO 98/28021 | 7/1998 |
| WO | WO 98/28024 | 7/1998 |

(List continued on next page.)

OTHER PUBLICATIONS

Arky, et al., *Physicians' Desk Reference*, 1997, pp. 1336–1340.

Mack Publishing Company, "Stability of Pharmaceutical Products," *Pharmaceutical Sciences*, pp. 1481–2, 1985.

(List continued on next page.)

*Primary Examiner*—Sharon Kennedy
(74) *Attorney, Agent, or Firm*—Kirton & McConkie; Michael F. Krieger

(57) ABSTRACT

An integrated apparatus for controlled heat aided dermal drug delivery is disclosed. The apparatus has a temperature control component and a drug delivery component. The temperature control component may and dermal drug delivery component are an integrated unit. The apparatus also comprises means to prevent exchange of substance(s) among the heat generating component, the drug delivery component and the outside environment. The apparatus is designed to be easy to use.

37 Claims, 3 Drawing Sheets

U.S. PATENT DOCUMENTS

| | | | |
|---|---|---|---|
| 4,495,402 A | * 1/1985 | Burdick et al. | 219/214 |
| 4,529,601 A | 7/1985 | Broberg et al. | 514/626 |
| 4,685,911 A | 8/1987 | Konno et al. | 604/897 |
| 4,693,706 A | 9/1987 | Ennis, III | 604/87 |
| 4,747,841 A | 5/1988 | Kuratomi et al. | 604/291 |
| 4,830,855 A | 5/1989 | Stewart | 424/448 |
| 4,898,592 A | 2/1990 | Latzke et al. | 604/307 |
| 4,911,707 A | 3/1990 | Heiber et al. | 424/449 |
| 4,913,957 A | 4/1990 | Strack et al. | 428/286 |
| 4,963,360 A | 10/1990 | Argaud | 424/443 |
| 4,994,049 A | 2/1991 | Latzke et al. | 604/307 |
| 5,046,479 A | * 9/1991 | Usui | 128/204 |
| 5,108,710 A | 4/1992 | Little et al. | 422/104 |
| 5,114,411 A | 5/1992 | Haber et al. | 604/203 |
| 5,128,137 A | 7/1992 | Müller et al. | 424/449 |
| 5,147,339 A | 9/1992 | Sundström | 604/307 |
| 5,169,384 A | * 12/1992 | Bosniak et al. | 604/20 |
| 5,213,129 A | 5/1993 | Someah et al. | 137/101.11 |
| 5,217,718 A | 6/1993 | Colley et al. | 424/449 |
| 5,229,133 A | 7/1993 | Wright et al. | 424/473 |
| 5,276,032 A | 1/1994 | King et al. | 514/239 |
| 5,279,594 A | 1/1994 | Jackson | 604/265 |
| 5,329,976 A | 7/1994 | Haber et al. | 141/25 |
| 5,330,452 A | 7/1994 | Zook | 604/307 |
| 5,364,350 A | 11/1994 | Dittman | 604/89 |
| 5,534,021 A | 7/1996 | Dvoretzky et al. | 607/112 |
| 5,580,573 A | 12/1996 | Kydonieus et al. | 424/449 |
| 5,605,536 A | 2/1997 | Sibalis | 604/20 |
| 5,626,571 A | 5/1997 | Young et al. | 604/370 |
| 5,651,768 A | 7/1997 | Sibalis | 604/20 |
| 5,658,583 A | 8/1997 | Zhang et al. | 424/402 |
| 5,662,624 A | 9/1997 | Sundstrom et al. | 604/291 |
| 5,728,057 A | 3/1998 | Ouellette et al. | 602/62 |
| 5,728,058 A | 3/1998 | Ouellette et al. | 602/62 |
| 5,728,146 A | 3/1998 | Burkett et al. | 607/109 |
| 5,733,255 A | 3/1998 | Dinh et al. | 604/20 |
| 5,735,889 A | 4/1998 | Burkett et al. | 607/96 |
| 5,741,318 A | 4/1998 | Ouellette et al. | 607/108 |
| 5,837,005 A | 11/1998 | Viltro et al. | 607/112 |
| D403,778 S | 1/1999 | Davis et al. | D24/206 |
| D403,779 S | 1/1999 | Davis et al. | D24/206 |
| 5,860,945 A | 1/1999 | Cramer et al. | 602/62 |
| D407,822 S | 4/1999 | Davis et al. | D24/206 |
| D407,824 S | 4/1999 | Davis et al. | D24/206 |
| D408,923 S | 4/1999 | Davis et al. | D24/206 |
| D409,757 S | 5/1999 | Davis et al. | D24/206 |
| 5,904,710 A | 5/1999 | Davis et al. | 607/108 |
| 5,906,637 A | 5/1999 | Davis et al. | 607/108 |
| 5,906,830 A | 5/1999 | Farinas et al. | 424/448 |
| 5,919,479 A | 7/1999 | Zhang et al. | 424/449 |
| 5,925,072 A | 7/1999 | Cramer et al. | 607/108 |
| D412,751 S | 8/1999 | Davis et al. | D24/206 |
| D417,283 S | 11/1999 | Davis et al. | D24/206 |
| 5,980,562 A | 11/1999 | Ouellette et al. | 607/108 |
| 5,984,995 A | 11/1999 | White | 75/230 |
| D418,606 S | 1/2000 | Davis et al. | D24/206 |
| 6,019,782 A | 2/2000 | Davis et al. | 607/96 |
| 6,020,040 A | 2/2000 | Cramer et al. | 428/64.1 |
| 6,024,761 A | 2/2000 | Barone et al. | 607/108 |
| 6,042,673 A | 3/2000 | Johnson et al. | 156/227 |
| 6,048,326 A | 4/2000 | Davis et al. | 602/26 |

FOREIGN PATENT DOCUMENTS

| | | |
|---|---|---|
| WO | WO 98/29063 | 7/1998 |
| WO | WO 98/29064 | 7/1998 |
| WO | WO 98/29065 | 7/1998 |
| WO | WO 98/29066 | 7/1998 |
| WO | WO 98/29067 | 7/1998 |
| WO | WO 99/09917 | 3/1999 |
| WO | WO 99/09918 | 3/1999 |

OTHER PUBLICATIONS

McCafferty, et al., "Comparative In Vivo and In Vitro Assessment of the Percutaneous Absorption of Local Anaesthetics," *British Journal of Anaesthesia*, vol. 60, (1988), 64–69.

Woolfson, et al., "Concentration–Response Analysis of Percutaneous Local Anaesthetic Formulations," *British Journal of Anaesthesia*, vol. 61, (1988), pp. 589–592.

McCafferty, et al., "In Vivo Assessment of Percutaneous Local Anaesthetic Preparations," *British Journal of Anaesthesia*, vol. 62, (1989), pp. 17–21.

Knutson et al., "Solvent–Mediated Alterations of the Stratum Corneum," *Journal of Controlled Release*, vol. 11, (1990), pp. 93–103.

Lycka, "EMLA, A New and Effective Topical Anesthetic," *J. Dermotol, Surg. Oncol.*, vol. 18, (1992), pp. 859–862.

McCafferty, et al., "New Patch Delivery System for Percutaneous Local Anaesthesia," *British Journal of Anaesthesia*, vol. 71, (1993) pp. 370–374.

Woolfson, *Percutaneous Local Anaesthesia*, E. Horwood, N.Y. (1993), pp. 166–170.

Astra USA, Inc., "EMLA Cream Product Information Form for American Hospital Formulary Service," (1993), pp. 1–28.

"Room Temperature," Macmillan, U.S.A., *Webster's New World College Dictionary*, Third Edition, 1997, p. 1165.

Florey, Klaus, *Analytical Profiles of Drug Substances*, vol. 15, 1986, pp. 150–231.

Florey, Klaus, *Analytical Profiles of Drug Substances*, vol. 12, 1983, pp. 73–105.

"Local Anesthetics, Parenteral, General Statement," *AHFS Drug Information*, 1992.

Florey, Klaus, *Analytical Profiles of Drug Substances*, vol. 18, 1989, pp. 379–411.

Sakamoto et al., "Dermal patch anaesthesia: comparison of 10% lignocaine gel with absorption promoter and EMLA cream," *Anesthesia*, (1993), vol. 48, pp. 390–392.

Dvoretzky, Israel, M.D., Hyperthermia Therapy for Warts Utilizing a Self–administered Exothermic Patch, *Dermal Surgery*, (1996), vol. 22, pp. 1035–1039.

Stern, Peter, M.D. and Levine, Norman, M.D., "Controlled Localized Heat Therapy in Cutaneous Warts," *Arch. Dermatol*, (Jul. 1992), vol. 128, pp. 945–948.

* cited by examiner

INTEGRATED APPARATUS FOR CONTROLLED HEAT AIDED DERMAL DRUG DELIVERY

RELATED APPLICATIONS

The present invention is a divisional application of U.S. patent application Ser. No. 09/162,890 filed Sep. 29, 1998 to Jie Zhang et al. entitled Apparatus and Methods for Improved Noninvasive Dermal Administration of Pharmaceuticals patent number now issued as U.S. Pat. No. 6,245, 347, which is a continuation-in-part of U.S. patent application Ser. No. 08/819,880 filed Mar. 18, 1997 to Jie Zhang et al. entitled Noninvasive Dermal Anesthetics patent number now issued as U.S. Pat. No. 5,919,479 which is a divisional of U.S. patent application Ser. No. 08/508,463 filed Jul. 28, 1995 to Jie Zhang et al. entitled Apparatus and Methods for Improved Noninvasive Dermal Administration of Pharmaceuticals patent number now issued as U.S. Pat. No. 5,658, 583.

BACKGROUND OF THE INVENTION

1. Field of the Invention

The present invention relates to an apparatus and method for facilitating temperature controlled dermal drug delivery. Specifically, the present invention relates to a configuration and use of an integrated temperature control device and a dermal drug delivery system. More specifically, the present invention relates to the configuration and use of an integrated layer of transdermally delivered drug formulation and a controlled heat aided drug delivery patch (hereinafter CHADD patch). The transdermally delivered drug formulation provides a non-invasive method for delivery of a therapeutic agent. The CHADD patch provides temperature control and facilitates dermal drug absorption. The present invention provides the convenience of an integrated dermal drug formulation and a CHADD patch while maintaining the stability of the CHADD patch and the drug formulation.

2. Relevant Technology

The dermal administration of pharmaceutically active compounds involves the direct application of pharmaceutically active formulations to the skin, wherein the skin absorbs a portion of the pharmaceutically active compound which is then taken up by the skin, tissues under the skin and the bloodstream. Such administration has long been known in the practice of medicine and continues to be an important technique in the delivery of pharmaceutically active compounds. For example, U.S. Pat. No. 4,286,592 issued Sep. 1, 1981, to Chandra Sicaran shows a bandage for administering drugs to a user's skin consisting of an impermeable backing layer, a drug reservoir layer composed of a drug and a carrier, and a contact adhesive layer by which the bandage is affixed to the skin.

For some drugs such dermal administration offers many important advantages over other delivery techniques, such as injection, oral tablets, and capsules. These advantages include being non-invasive, avoiding first pass metabolism of the drug in the liver when the drug is taken orally and absorbed through the gastrointestinal tract, and in some instances, avoiding undesired high peaks and low valleys of concentration of pharmaceutically active compounds in the patient's bloodstream. Other possible advantages include: avoidance of a harsh environment in the stomach, reduced total dosage, reduced cost in some instances, and improved compliance with prescribed use.

The term "dermal drug delivery system" or "DDDS", as used herein, is defined as an article, apparatus, or method for administering pharmaceutically active compound(s) for delivery into the skin, the regional tissues under the skin, the systemic circulation, or other targeting site(s) in a human body via skin permeation. The term "DDDS" in this application, unless otherwise specified, only refers to those systems in which the main driving force for drug permeation is the drug concentration gradient (passive permeant).

The term "skin," as used herein, is defined to include stratum corneum covered skin and mucosal membranes.

The term "drug," as used herein, is defined to include any pharmaceutically active compound, including but not limited to, compounds that treat diseases, injuries, undesirable symptoms, and improve or maintain health.

In DDDSs, a drug(s) is usually contained in a formulation, such as a hydro-alcohol gel, and may include a rate limiting membrane between the formulation and skin for minimizing the variation in the permeation of the drug. When a DDDS is applied to skin, the drug begins to transport out of the formulation, and transport across the rate limiting membrane (if present). The drug then enters the skin, enters blood vessels and tissues under the skin, and is taken into the systemic circulation of the body by the blood. At least some DDDSs have certain amounts of pharmaceutically active compound in or on the skin side of the rate limiting membrane (if present) prior to use. In those DDDSs, that portion of the drug on the skin side of the rate limiting membrane will enter the skin without passing through the rate limiting membrane. For many drugs, a significant portion of the dermally absorbed drug is stored in the skin and/or tissues under the skin (hereinafter referred as "depot sites") before being gradually taken into the systemic circulation (hereinafter referred to as "depot effect"). This depot effect is believed to be at least partially responsible for the delayed appearance of the drug in the systemic circulation after the application of some DDDSs and for continued delivery of the drug into the systemic circulation after the removal of some DDDSs from the skin.

After placing a DDDS on the skin, the drug concentration in the targeted tissue or blood typically remains at or near zero for a period of time, before starting to gradually increase and reach a concentration deemed to be medicinally beneficial, called the "therapeutic level" (the time it takes to reach the therapeutic level is referred to hereinafter as the "onset time"). Ideally, the concentration of the drug in the targeted tissue or blood should plateau (i.e., reach a substantially steady state) at a level slightly higher than the therapeutic level and should remain there for extended period of time. For a given person and a given DDDS, the "concentration of the drug in the targeted tissue or bloodstream vs. time" relationship usually cannot be altered under normal application conditions.

The onset time and the delivery rate of the drug into the targeted area(s) of the body for a typical DDDS are usually determined by several factors, including: the rate of release of the drug from the formulation, the permeability of the drug across the rate limiting membrane (if a rate limiting membrane is utilized), the permeability of the drug across the skin (especially the stratum corneum layer), drug storage in and release from the depot sites, the permeability of the walls of the blood vessels, and the circulation of blood and other body fluid in the tissues (including the skin) under and around the DDDS. Although these primary factors affecting onset time and delivery rate are known, no existing DDDS is designed to have alterable delivery rate in the course of the application of the drug and therefore no existing DDDS is able to provide for example, an increased concentration of a pharmaceutically active compound in a patient's bloodstream for a short period of time (a narrow peak) in the course of the application of a DDDS, when it is desirable to do so.

While a DDDS works well in many aspects, current dermal drug delivery technology has some serious limitations, including: 1) the onset time is undesirably long for many DDDSs; 2) the rate that the drug is taken into the systemic circulation or the targeted area(s) of the body cannot be easily varied once the DDDS is applied onto the skin and, when the steady state delivery rate is achieved, it cannot be easily changed; and 3) the skin permeability is so low that many drugs are excluded from dermal delivery because the amount of drug delivered is not high enough to reach a therapeutic level. In addition, temperature variations in the skin and the DDDS are believed to contribute to the variation of dermal absorption of drugs.

It is known that elevated temperature can increase the absorption of drugs through the skin. U.S. Pat. No. 4,898,592 issued Feb. 6, 1990 to Latzke et al., relates to a device for the application of heated transdermally absorbable active substances which includes a carrier impregnated with a transdermally absorbable active substance and a support. The support is a laminate made up of one or more polymeric layers and optionally includes a heat conductive element. This heat conductive element is used for distribution of the patient's body heat such that absorption of the active substance is enhanced. U.S. Pat. No. 4,230,105, issued Oct. 28, 1980 to Harwood, discloses a bandage with a drug and a heat-generating substance, preferably intermixed, to enhance the rate of absorption of the drug by a user's skin. Separate drug and heat-generating substance layers are also disclosed. U.S. Pat. No. 4,685,911, issued Aug. 11, 1987 to Konno et al., discloses a skin patch including a drug component, and an optional heating element for melting the drug-containing formulation if body temperature is inadequate to do so.

While it is known that elevated temperatures can increase the absorption of a drug through the skin, the use of a separate heating element in the administration of dermal drug delivery systems to increase the absorption of drugs through the skin may present a number of disadvantages (when compared with a dermal drug delivery system having an integrated temperature control component). For example, the use of a separate temperature control element can complicate the administration of the therapeutic agent by requiring the patient or care giver to take additional steps to employ the temperature control element, such as acquiring, storing and preparing the separate temperature control element and the administrating and removing the separate temperature control element.

Also, as the complexity of administrating the therapeutic agent increases, the likelihood of compliance by the patient or caregiver with the prescribed use of the temperature control element tend to decrease, potentially reducing the effectiveness of the prescribed treatment. If the prescribed use requires a patient to purchase, store, prepare, administer and then remove a separate heating element in addition to administering a DDDS, the patient may feel inconvenienced by the additional time and choose to forego the prescribed use of the separate temperature control element. Furthermore, the use of a separate temperature control element is limited by the compatibility between a given temperature control element and the DDDS with which the temperature control element is to be used. The shape, formulation and configuration of the DDDS may prevent effective use of a separate heating element, where the separate heating element is not specifically designed for use with the DDDS.

While there are disadvantages to the use of a separate temperature control element with a DDDS, combining the two without careful consideration may be difficult and problematic. For example, one could attempt to combine the temperature control element with a DDDS by making the drug formulation in the DDDS capable of generating heat when exposed to oxygen or by another mechanism. However, in order to do so it would be necessary for the heat generating medium and the drug formulation to be completely compatible with each other. When using an exothermic oxidation reaction to generate heat, if the heat generating medium comprising iron powder, activated carbon and water is mixed with an aqueous gel-based local anesthetic formulation, it cannot generate heat properly because, among other reasons, the gel in the local anesthetic formulation would prevent oxygen from entering the heat generating medium.

Another approach which initially appears straightforward would be simply affixing a CHADD patch onto a drug patch, and placing the integrated patch into an air-tight container. This approach was utilized by Albert Argaud in U.S. Pat. No. 4,963,360. The Argaud patent teaches the use of a base sheet to which is applied on one side a gelatin layer holding the medication, and on the other side a composition designed to have a exothermic reaction when exposed to air. Because there is no heat regulating mechanism in the Argaud patent, the absorption of the medicinal component will not be controlled. Uncontrolled absorption can cause serious reactions in patients due to drug overdose and under dose. These attendant side affects out weigh the benefits provided by the exothermic reaction. In addition, to the problems of regulating the heat in these early DDDS's, other problems such as the lack of any insolation or any engineering to direct the heat into the body also reduce the effectiveness and consistency of the exothermic reaction.

Since these early patches also did not provide for a mechanism for sealing the medicinal layer against the skin, rapid evaporation of the medicinal component can occur once the gel is exposed to air. Moreover, without a means to affix the patch securely to the skin, there is no assurance of proper absorption. As can be seen by looking at the example provided by the Argaud reference, there is a limited contact area between the medicinal layer and the contact area is likely to vary, affecting the amount of drug absorbed. Another problem with the Argaud patch is that because of the packaging of the device, the air within the package is allowed to communicate with both the drug formulation and heat generating medium. This approach allows the exchange or transfer of substance(s) between the heat generating medium and the drug formulation during storage, which may compromise either or both the drug formulation and the heat generating medium. For instance, if the heat generating medium has a proper ratio of iron powder, activated carbon, salt, wood powder and water and the drug formulation is in the form of a hydrogel, the heat generating medium may absorb water vapor from the drug formulation, and thus change the desired concentrations of water in both the heat generating medium and the drug formulation. This problem as it applies to the use of fentanyl is explained in greater detail below.

The difficulty of combining a temperature control unit with a DDDS is illustrated by the following example of combining a CHADD oxidation patch with a fentanyl DDDS. By affixing a heating component having a heat generating medium as described in the paragraph above disposed to a fentanyl patch having a formulation containing alcohol and water (similar to the formulation in Duragesic patches), one could attempt to form an integrated patch, and this integrated patch could be sealed in an air-tight container. Although the air-tight container would separate the integrated patch from the outside environment, and although a barrier film may be placed between the CHADD heating component and the drug formulation, the alcohol and water in the fentanyl formulation could still migrate into the space in the air-tight container is the form of vapors and be absorbed into the heat generating medium. The activated carbon in the heat generating medium has a strong tendency to absorb volatile substances. Therefore over time, the fentanyl formulation would lose a significant amount of alcohol and water.

Both alcohol and water play very important roles in the transdermal delivery of fentanyl. At least one function of alcohol in the formulation is to increase skin permeability, so that the desired amount of fentanyl can be absorbed. Water and alcohol also serve as the solvent of fentanyl in the formulation. If a temperature control apparatus and a fentanyl DDDS are combined as explained in the paragraph above, significant amounts of alcohol and water would be lost during storage and skin permeability would not be increased as designed, leading to lower dermal absorption of fentanyl. In addition, fentanyl solubility and concentration in the formulation would be changed, which would change the driving force for transdermal fentanyl permeation. As a result, fentanyl absorption from the transdermal patch would likely be quite different from the designed rates and be quite unpredictable. This could cause serious drug under dose or overdose.

Furthermore, if enough alcohol and water are absorbed into the heat generating medium, the function of the heating component may also be compromised. In a heat generating medium using activated carbon, the activated carbon has a tendency to absorb moisture from the surrounding environment. If the water quantity in the heat generating medium is increased too much, the heat generating medium will not generate heat properly. Thus it is important to shield the heat generating medium from moisture. It is similarly important to protect the heat generating medium from exposure to oxygen to prevent the oxidation reaction from transpiring prematurely.

Thus, it is very important to have good separation between the drug formulation and the heating component in an integrated patch, even if the integrated patch is sealed in an air-tight container. This separation should not only prevent direct transfer of substance(s) between the drug formulation and the heating component (i.e., permeation) but also prevents the transfer or exchange through vapor via the space in the airtight container. It would therefore be an advancement in the art to provide a configuration that combines the convenience and ease of use of an integrated temperature control component with a dermal drug delivery component that can simultaneously prevent undesired transfer of substance(s) between the temperature control component and dermal drug delivery system, shields them as necessary from ambient oxygen and undesired solvents, and prevents undesired gain or loss of the solvent to the environment.

OBJECTS AND BRIEF SUMMARY OF THE INVENTION

In view of the foregoing, it is an object of some of the embodiments of the present invention to provide a dermal drug delivery system (DDDS) which integrates a temperature control component with a dermal drug delivery component, thereby allowing for reduced complexity and redundancy in manufacturing, distributing and storing of the system, while preventing transfer of substance(s) among the components and the outside environment.

It is another object of some embodiments of the present invention to provide a DDDS which integrates a temperature control component with a dermal drug delivery component, thereby allowing the integrated components to be stored in one container, while preventing transfer of substance(s) among the components and the outside environment.

It is yet another object of some embodiments of the present invention to provide a DDDS which integrates a temperature control component with a dermal drug delivery component, thereby allowing for greater convenience of use than the use of a separate temperature control element and dermal drug delivery system while preventing transfer of substance(s) among the components and the outside environment.

It is still another object of some embodiments of the present invention to provide a DDDS which integrates a temperature control component with a dermal drug delivery component, thereby promoting patient compliance with prescribed use, while preventing transfer of substance(s) among the components and the outside environment.

It is further an object of some embodiments of the present invention to provide a DDDS which integrates a temperature control component with a dermal drug delivery component that conveniently combines the components and prevents oxygen and ambient air from flowing into the heat generated medium during storage.

It is yet another object some embodiments of the present invention to provide a DDDS which integrates a temperature control component with a dermal drug delivery component that conveniently combines the components and prevents absorption of moisture in ambient air into the temperature control component or into the drug delivery component while in storage.

It is a still further object of some embodiments of the present invention to provide a DDDS which integrates a temperature control component with a dermal drug delivery component that conveniently combines the components and prevents absorption of the ingredients into the drug formulation and into the temperature control component while in storage.

It is yet another object of some embodiments of the present invention to provide a DDDS which integrates a temperature control component with a dermal drug delivery component that conveniently combines the components and limits undesired interaction between the components while in storage.

It is also an object of some embodiments of the present invention to provide a DDDS which integrates a temperature control component with a dermal drug delivery component that conveniently combines the components and maintains a proper ratio of ingredients in a temperature control component and in a drug delivery component while in storage.

It is another object of some embodiments of the present invention to provide a DDDS which integrates a temperature control component with a dermal drug delivery component that conveniently combines the components and prevents significant modification of the components while in storage.

It is another object of some embodiments of the present invention to provide a DDDS which integrates a temperature control component with a dermal drug formulation applicator thereby facilitating the application of therapeutic agents which are not practically stored in combination with the temperature control component.

The present invention integrates a drug delivery component, such as a transdermal drug delivery system, with a temperature control component, such as a CHADD patch. The drug delivery component comprises a drug formulation applicator and a drug formulation secured to the drug formulation applicator. A barrier and/or compartment prevents undesired substance(s) transfer between the temperature control component and the drug delivery component. A barrier and/or compartment also prevents exchange transfer or absorption of volatile substances between the drug delivery and temperature control components and the external environment. The temperature control component comprises a temperature modification element and a temperature control which can control or adjust the heat generated by the temperature modification element.

The drug delivery component may be similar to known dermal drug delivery systems having a drug disposed within a formulation, the formulation adhering to or contained within a drug applicator. A drug formulation applicator can be any structure or process in a dermal drug delivery system which facilitates or results in the delivery of the drug or drug formulation to the skin of a patient, for example, a gauze pad secured to adhesive tape. The drug applicator may include a rate limiting membrane between the drug formulation and the user's skin, or alternatively the formulation may be in direct contact with the skin. A physical barrier, such as an impermeable medical packaging film, provides means for preventing exchange or substance(s) between the drug delivery component and the temperature control component via direct permeation or vapor absorption. The drug applicator with the drug formulation are secured to the means for preventing exchange. This drug delivery component is integrated with the temperature control component to form the integrated patch. Additionally, a layer of medical adhesive tape may be secured to the barrier film or other part of the integrated patch, thereby providing means for attaching the integrated patch to the skin of the patient.

The absorption of the therapeutic drug is usually determined by a number of factors including: the diffusion coefficient of drug molecules in the drug formulation, the permeability coefficient of the drug across a rate limiting membrane (if any), the concentration of dissolved drug in the formulation, the skin permeability to the drug, the body fluid (including blood) circulation in the skin and/or other tissue under the skin, permeability of the walls of capillary blood vessels in the sub-skin tissues and absorption into and release from depot sites in the sub-skin tissues. It is believed that controlled heating can potentially affect each one of the above factors, and thus, it is desirable to have a temperature control component integrated with a drug delivery component.

The integrated patch of the present invention provides for the use of a wide variety of drug formulations. The formulation itself may take various forms such as liquid, gel, cream, paste, or solid. Generally, a therapeutic agent is mixed or dissolved into the drug formulation. The drug delivery system of the present invention contemplates the use of a transdermally administered drug in a drug formulation including, but not limited to, drugs such as analgesics, androgens, anesthetics, and anesthetic agents. The drug formulation applicator is configured to hold the drug formulation such that the drug formulation on the applicator can be easily removed from its storage pocket and administered to a patient's skin.

The temperature control component has a temperature modification element which may be a heat generating element (for example, a CHADD patch) and a temperature control, to allow the user to adjust the temperature. CHADD patches are specifically designed to improve the efficiency and therapeutic effectiveness of dermal drug delivery systems. An important feature of the CHADD patch is that it can quickly increase skin temperature to a temperature around 39° C.–43° C. The CHADD patch can maintain skin temperature in that range for an extended period of time. This not only provides consistent heating, but also prevents skin damage which could be caused by over heating when using other heating methods.

One embodiment of the CHADD patch comprises a shallow chamber defined by a bottom, a frame wall, and a cover. Within the shallow chamber is a heat generating medium which, upon contact with ambient oxygen, can generate heat. The chamber has a cover which is made of a material impermeable to oxygen. The cover has areas which are open to allow oxygen into the chamber. The openings maybe selectively covered, partially covered, or opened by the user to control air flow into the chamber and the heat generated therein. Alternatively, certain or all areas of the cover may be covered by a membrane with certain permeability to air. Thus the cover can allow ambient air to flow into the chamber at a desired rate, which in turn causes the oxidation reaction in the heat generating medium to generate a desired temperature on the skin. The bottom of the chamber and frame wall are also substantially impermeable to oxygen. Within the chamber the heat generating medium which generally comprises activated carbon, iron powder, salt, and water. Agents that improve air flow, such as fine wood powder may also be added. The ratio of components in this embodiment is very important in order for the heat generating medium to work properly. For example, a typical ratio of approximately 5:16:3:2:6 of activated carbon:iron powder:fine wood powder:sodium chloride: and water (all weights) makes a reasonably good heat generating medium.

The CHADD patch which uses an oxidation reaction to generate heat needs to be stored in an air-tight container. When the patch is removed from the container, oxygen in the ambient air flows into the shallow chamber, initiating a heat generating oxidation reaction in the heat generating medium. The amount of heat generated per unit of time is controlled by the rate of the oxygen flow into the heat generating medium through the cover. Less than the entire number and size of holes on the cover can be utilized to further control the amount of heat generated per unit of time.

Effectively, combining a CHADD patch as a temperature control component with a dermal drug delivery component such as briefly described above, results in an integrated dermal drug delivery system patch (hereinafter "integrated CHADD patch").

The integrated CHADD patch design allows a person or care giver to more conveniently apply controlled heat for the purpose of more effective transdermal drug delivery. Additionally, the integrated CHADD patch design helps to prevent the misuse or improper use of controlled heat with transdermal drug delivery. The integrated patch provides for a more uniform heating of the associated drug formulation. When a patient uses a drug delivery system with a separate temperature control element, it is possible that improper placement of the temperature control element by the user or unintended displacement of the heating element may result in uneven heating of the drug formulation. A separate temperature control element requires the patient or care giver to determine which kind of element to use, when to initiate heating, when to terminate heating, what temperature range is appropriate, and where and how to direct or attach the heat from the separate temperature control element. The actual handling may vary from patient to patient and treatment to treatment. A patient or care giver could easily make the wrong decision concerning the issues listed above and thus misapply the separate heating element. Improper use of the temperature control element may yield improper drug dosage. The integrated heat component and drug delivery component help to reduce or eliminate the potential for misuse of a separate temperature control element.

A preferred embodiment of the integrated CHADD dermal drug delivery patch comprises a tray made of a material that is a good barrier to volatile liquid, especially water, and alcohol but not necessarily a good barrier to oxygen. The tray defines a shallow reservoir capable of accommodating both a drug formulation and drug formulation applicator. The drug formulation adheres to the drug formulation applicator. The drug formulation applicator is secured to a film which is a good barrier to volatile liquids. The film can be heat sealed to the edge of the tray to form a closed compartment defined by the reservoir within the tray and the film. The drug formulation resides within the compartment. Since both the tray and lid to the compartment act as barriers to solvents, when the compartment is sealed tight, it prevents the transfer of substance(s) between the drug formulation and the outside environment.

On top of the film is an adhesive tape that has an area slightly larger than the film. The adhesive side of the adhesive tape faces the film and the edges of the tape extend out beyond the edges of the film. The portion of the adhesive tape which extend beyond the edges of the film is used to secure the integrated patch to the skin of the user. The CHADD patch is secured on top of the adhesive tape, and is centered on the adhesive tape. It is desirable that the inside area of the CHADD patch containing the heat generating medium be substantially the same or slightly larger than the area of the drug formulation applicator, to provide for effective heating. In other words, when the CHADD patch is secured to the film barrier and drug applicator, the heat generating element should be present directly above any areas of drug formulation so that substantially all of the drug formulation (which is also the barrier film) is evenly and uniformly heated.

In the preferred embodiment, the outer-most edges of the lidding film are not sealed onto the tray, and an adhesive tape is placed on top of the lidding film with the adhesive side adhered to the lidding film. The size of the adhesive tape may be similar to that of the lidding film, or preferably, slightly larger than the lidding film. If the adhesive tape is slightly larger than the lidding film, the portion of the adhesive tape that extends beyond the edges of the lidding film is rested on the tray. When a patient is removing the tape from the tray for use, the adhesive tape can be peeled from the tray at one end. The portion of the lidding film that is not sealed onto the tray (but is adhered to the adhesive tape) comes up with the adhesive tape. As the peeling continues, the entire lidding film, and the drug formulation attached to it, comes up with the adhesive tape. The adhesive tape, with the CHADD patch on the upper side and the drug formulation in the lower side, is then used to affix the integrated patch onto the skin. The tray may be indented at the end(s) to facilitate the start of the peeling.

The integrated patch is sealed in an air-tight container. The formulation is completely sealed in the space between the tray and the barrier film, so no exchange of substances between the formulation and the heat generating medium or the outside environment may take place. The heat generating medium is further sealed by the air-tight container so it is completely contained in the space inside the air-tight container. Thus the drug formulation is completely isolated from both the temperature control component and the outside environment. The temperature control component is isolated from the drug formulation. When the integrated patch is sealed into an air-tight container, the temperature control component is also isolated from the outside environment. Thus, the CHADD patch can be integrated with the drug delivery component and can be stored together in an air tight compartment such as a pouch made of film which is a good barrier to both air and moisture.

In one embodiment of the integrated DDDS patch, the barrier for preventing undesired substance transfer between the drug delivery system component and the temperature control component may comprise one or more chambers or compartments in which the drug delivery component and temperature control component are isolated while remaining structurally integrated. The chambers may be impermeable substances as required by the specific drug formulation and temperature control component. Similarly, means for preventing transfer of substances between the drug delivery and temperature control components with the external environment may comprise a chamber or pouch in which the integrated CHADD patch is stored. The chamber or pouch may be impermeable to moisture, oxygen, light or other environmental factors as necessary.

In one embodiment of the integrated CHADD patch, means for preventing undesired heat loss is provided. Means for preventing undesired heat loss includes insulating materials used in the drug delivery and temperature control components. Other means for preventing undesired heat loss include using adhesives and other means for securing and sealing the integrated DDDS patch to the skin of the user so that heat does not escape through unsecured edges or corners of the drug delivery component and temperature control component, as well as customized shaping or molding of the integrated CHADD patch to more appropriately fit a specific part of the user's body.

In one embodiment of the present invention, a means for preventing undesired heat loss is provided. In some instances it can be difficult to secure a corner of a patch to a user's skin. FIG. 4 shows an integrated CHADD patch having a substantially oval shape. The oval shape does not have corners, as would a rectangular or square shaped patch. Thus the oval shape facilitates the prevention of heat loss through unsecured corners by eliminating corners which may be difficult to secure and result in undesired heat loss.

Another embodiment of the present invention provides a foam cover for the heat generating component. The foam tape cover has insulative properties which help to minimize heat loss through the cover and which help to prevent varying ambient temperatures from adversely affecting the heat generated by the CHADD component. Moreover, an insulative cover capable of insulating the exposed surfaces of the integrated CHADD patch is also contemplated.

It is often necessary for the heat generating medium and the drug formulation to be entirely sealed from each other and from the external environment during storage and/or use. It is also desirable to provide convenient application and use of both components despite the sophisticated sealing necessary to preserve the drug formulation and heat generating medium. The novel configurations in this invention provide both satisfactory separation of the components during storage and/or use, and convenience in application and use.

The temperature control component and the drug delivery component of the present invention are preferably isolated. The isolated drug delivery component and the isolated temperature control component are disposed to prevent or avoid undesired interaction with the environment and with other components of the device. For example, the isolated temperature control component can be an exothermic medium enclosed in a substantial air-tight environment having a barrier which prevents undesired substance transfer among the heat generating medium in the temperature control component, the environment and the drug delivery component. Similarly, the isolated drug delivery component may be enclosed in a substantially air-tight compartment and may have a barrier to prevent any undesired substance transfer or exchange among the outside environment, the temperature control component and the drug delivery component. Isolation requirements for each component may differ depending upon the heat generating medium and the drug formulation being used.

Without careful designing, attempts to combine heat produced by exothermic oxidation reactions and transdermal drug delivery may result in an inoperative or ineffective combination. Some are rendered inoperative or ineffective because the components are not properly and conveniently isolated. Substances from the drug formulation may be lost to and/or foul the heat generating oxidation reaction elements through vapor absorption. During storage, the loss of substance(s) from the drug formulation may cause the drug formulation to function significantly differently than originally desired. Furthermore, substance(s) from the temperature control component may undesirably interact with the drug formulation rendering it less effective or ineffective. Other combinations are difficult or impractical to produce and use.

BRIEF DESCRIPTION OF THE ILLUSTRATIONS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
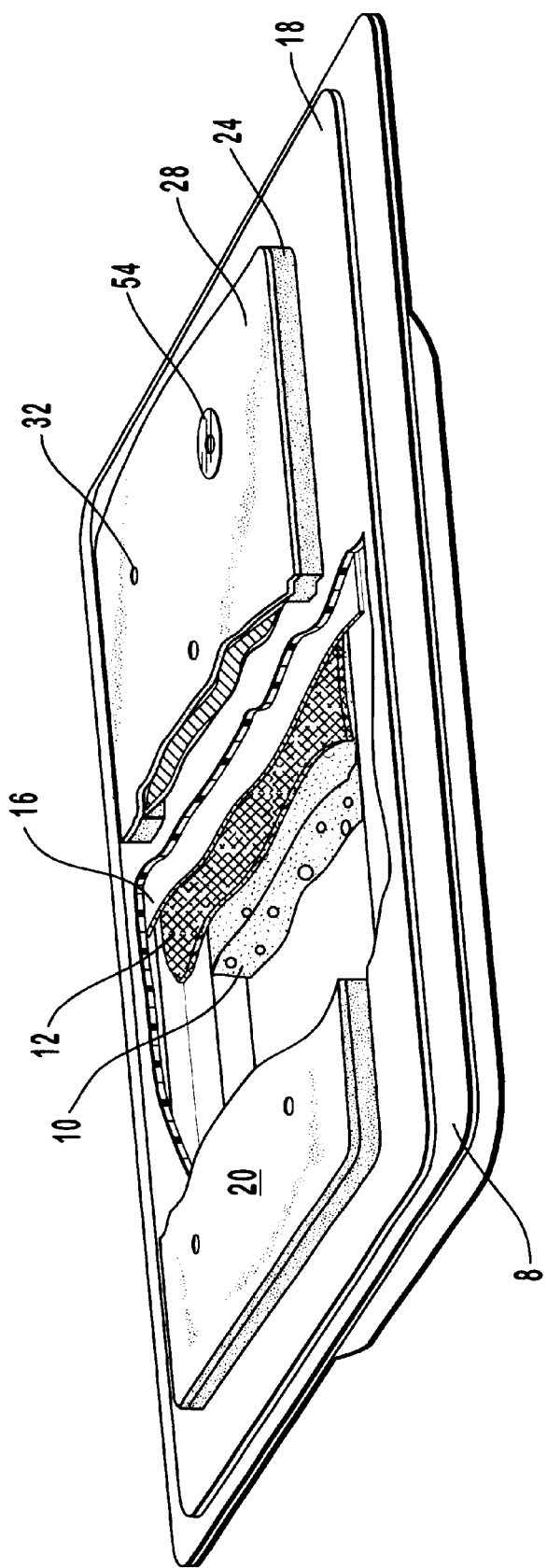
FIG. 1 shows a perspective view of a layered cut away of one embodiment of the integrated patch.
Figure 2:
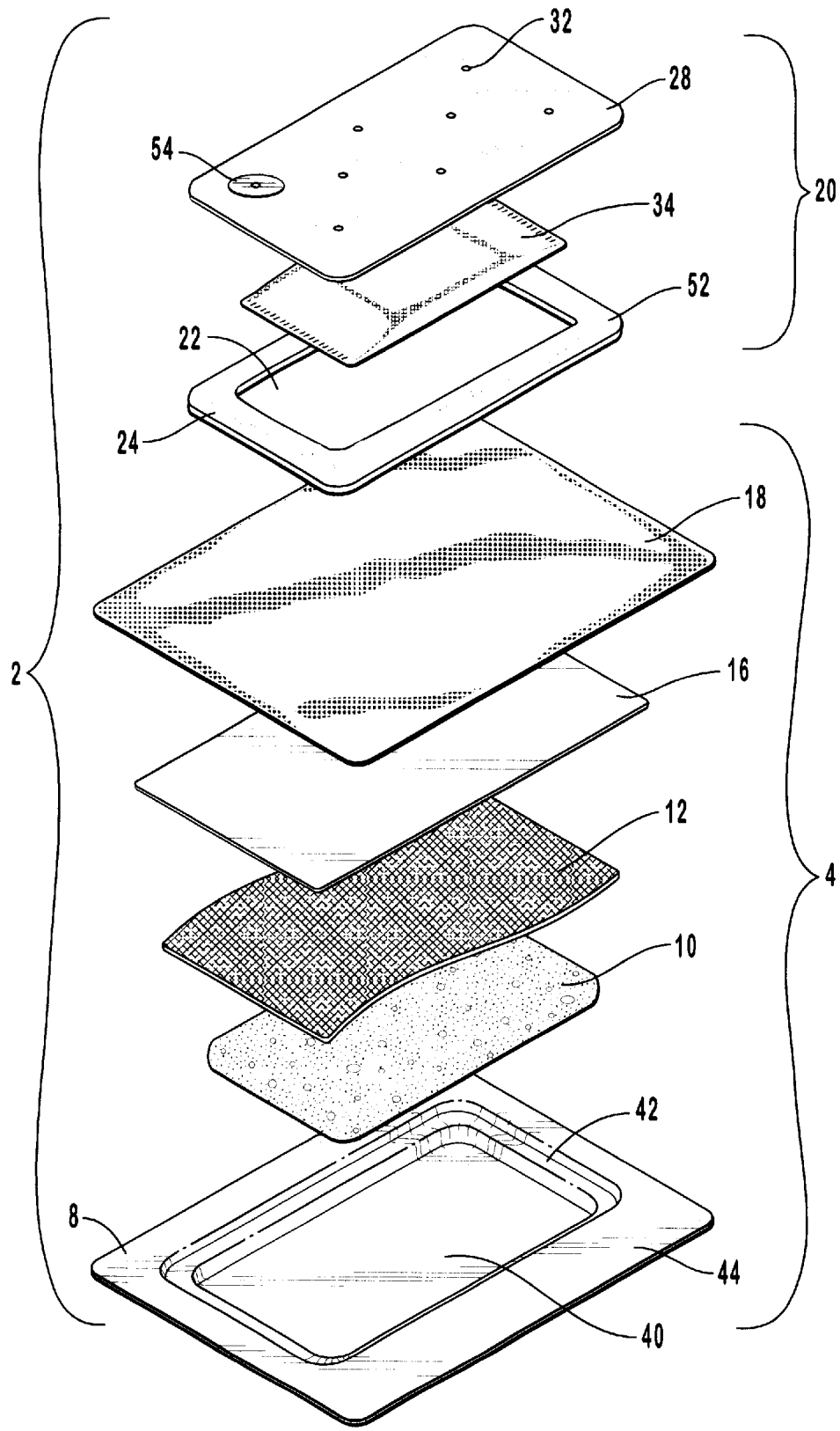
FIG. 2 shows an exploded view of the integrated patch in FIG. 1.
Figure 3:
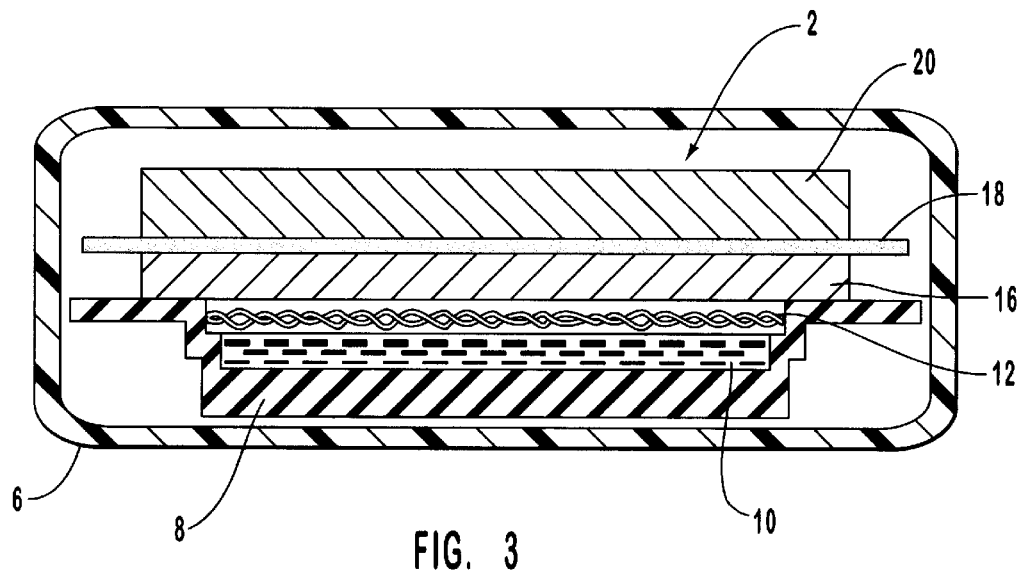
FIG. 3 shows the patch in FIG. 1 in cross-section as stored.

FIGS. 1–3 illustrate various views of the integrated patch. The integrated patch 2 comprises a temperature control component 20 and a drug delivery component 4. The integrated patch 2 is stored within a foil pouch 6.

The drug delivery component 4 further comprises a tray 8 defining a drug formulation reservoir 40 and a drug applicator reservoir 42 substantially co-extensive with drug formulation reservoir 40. Tray 8 has a rim 44 extending around its perimeter. Drug formulation 10 is disposed within formulation reservoir 40 of tray 8. Gauze 12 is disposed within applicator reservoir 42 and is in contact with the drug formulation 10 disposed within formulation reservoir 40. Film barrier 16 is releaseably secured to rim 44 of tray 8 and secured to gauze 12. Film barrier 16 secured to rim 44 of tray 8 defines a drug formulation compartment. Adhesive tape 18 is releaseably secured to the rim 44 of tray 8 and is secured to the top of film barrier 16. Tape 18 is wider and longer than film 16, gauze 12 and drug formulation 10 such that adhesive tape 18 extends beyond the perimeters of film 16, gauze 12 and drug formulation 10. Adhesive on the bottom side of tape 18 is used to secure the integrated patch to the skin of the user and to secure tape 18 to tray 8.

The temperature control component 20 is further comprised of a patch reservoir 52. The patch reservoir may be defined by a medical tape base 22, a foam tape frame 24 and a foam tape cover 28. Heat generating medium 34 is disposed within patch reservoir 52. Cover 28 defines a plurality of holes 32. Holes 32 can be selectively covered and uncovered with an oxygen impermeable or air flow rate limiting hole cover 54. Hole cover 54 allows the permeability of cover 28 to be selectively adjusted by covering and uncovering some or all of holes 32 or by varying the duration that the holes are uncovered. Holes 32 may be covered with a membrane (not shown) having select air permeability.

3. Relevant Technology

In the preferred embodiment means for isolating the drug delivery component is a compartment defined by film barrier 16 and tray 8. Other means for isolating the component degradation of the drug delivery component may include alternative physical barriers.

The preferred embodiment illustrated in FIG. 3 shows a means for isolating the temperature control component comprising a foil pouch 6. Other means for isolating the component from external environmental factors include alternative physical barriers, for separating integrated patch components from the environment.

One embodiment shown in FIG. 2 shows a temperature control component 20 comprising holes 32 defined in the non-permeable cover 28, holes 32 being selectively coverable and uncoverable. Other means for controlling the temperature are contemplated relative to the heat generating medium 34 in the temperature control component 20. Such alternative means would include electronic means for adjusting temperatures and alternative methods for controlling heat generated by exothermic reaction rates (i.e. ambient oxygen is let into the heat generating medium through the frame wall).

In the preferred embodiment illustrated in FIG. 2 the temperature modification element is a heat generating medium 34, more specifically a medium capable of undergoing an exothermic oxidation reaction with oxygen. Other temperature modification elements are also contemplated such as an electronic heat generating element and alternative exothermic chemical reactions.

Figure 4:
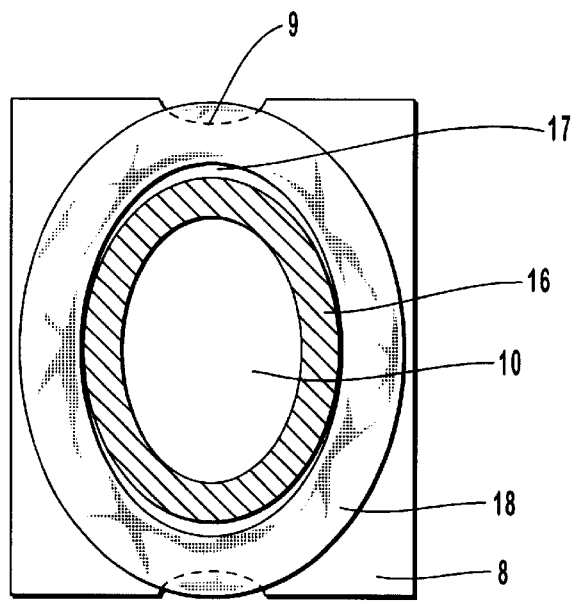
FIG. 4 shows a top, transparent view of the drug delivery component of one embodiment of the integrated patch.
Figure 5:
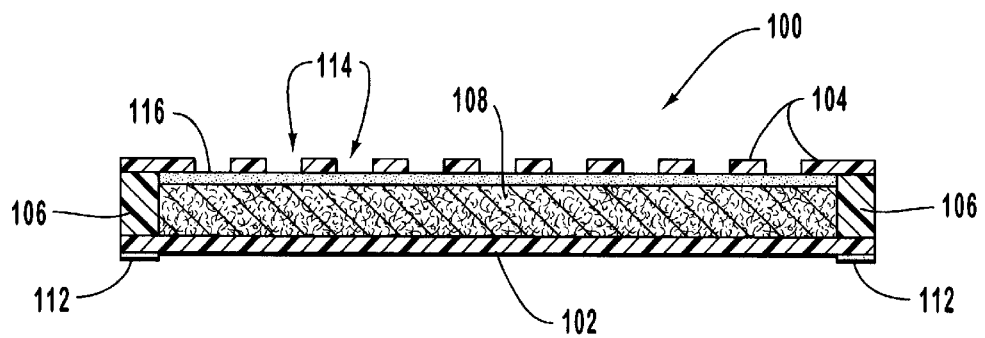
FIG. 5 shows a cross section of a CHADD patch.

The relative positioning of the adhesive tape and the barrier film as well as the relative strength of the adhesive and the heat sealing are taken into account in order to provide easy removal of the patch from the tray at tab 9 without unintentionally disassembling the integrated patch 2. As shown in FIG. 4, it is preferred that of the heat sealable film 16 have at least one end 17 remain unsealed to the tray, but adhered to the adhesive tape. This allows the heat sealable film 16 to be removed with the adhesive tape, rather than remaining secured to tray 8. In the embodiment shown in FIG. 4, it has been found that it is suitable to terminate the heat sealing bond approximately 2 mm from the narrow end of the film 16.

EXAMPLE 1

In an actual embodiment of the present invention, an integrated patch 2 was comprised of local anesthetic delivery component 4 and heating component 20. Local anesthetic delivery component 4 comprised a tray 8 having a width of about 2.5 inches and length of about 3.0 inches, the tray being composed of high density polyethylene (HDPE). Tray 8 defined a formulation reservoir 40 having a lower area in an otherwise substantially flat tray. An area on the tray, a ring (about 0.2 mm in width) surrounding the reservoir is slightly lower then the flat area of the tray that accommodates the gauze. Reservoir 40 had a width of about 1 inch, a length of about 1.65 inches and a depth of about 1 millimeter. Tray 8 possessed good barrier properties which inhibited the transfer of substance between the formulation in said reservoir in tray 8 and the environment on the other side.

The local anesthetic formulation, about 1 gram, was disposed within formulation reservoir 40 and which covered the entire area of reservoir 40. The formulation had the following weight composition: 1:1 (w:w) lidocaine base; tetracaine base eutectic mixture: 14%; polyvinyl alcohol: 10.3%; lecithin: 2.6%; water: 73.1%. The formulation was a white, viscous fluid.

A gauze pad 12, about 1.08 inches by 1.70 inches in dimensions and impregnated with about 10 mg boric acid, sodium salt was placed on the formulation in the reservoir. The boric acid, sodium salt in the gauze pad then diffused into the formulation and caused the formulation to form a solid gel (as polyvinyl alcohol in the formulation was cross linked by boric acid, sodium salt).

A heat sealable barrier film 16 having a width of about 1.5 inches and a length of about 2.125 inches was placed on top of the gauze 12 and sealed onto tray 8. The barrier film 16 (Perfecseal 35786G) had excellent barrier properties to oxygen and moisture. The heat sealing area was such that (1) the edges of the gauze over-extending the formulation were sealed onto the barrier film 16 securing the gauze 12 to the film; (2) all the area of the barrier film extending beyond the gauze was sealed onto tray 8, with the exception that a leading edge 11 of at least one side of the barrier film 16 was not sealed onto tray 8, in order to provide a leading edge for peeling. The barrier film 16 and tray 8 thus formed a closed chamber for the formulation. The chamber had good barrier property in all directions so that the transfer of substances between the formulation and the outside environment was avoided.

An adhesive tape 18 (3M 1527-2) with length and width slightly larger than the barrier film was placed on to tray 8 and the barrier film 16, with the adhesive side adhered to the barrier film and tray 8.

Heating component 20 comprised a chamber defined by a surrounding wall made of a closed-cell foam tape (3M 1779), a bottom made of an adhesive tape (3M 1525L) with the nonadhesive side facing the inside of the chamber, and a foam tape (3M 9773) cover 28 with 8 holes (diameter about 1/16 inch) covered by a microporous membrane (3M CoTran 9711). The outside dimensions of the chamber were about 1.5 inches in width, 2.125 inches in length, and 3/16 inches in thickness. The inside dimensions of the chamber were about 1.0 inch in width, 1.625 inches in length and 1/8 inch in thickness. All corners were rounded. Inside the chamber was a heat generating medium 34 comprising iron powder, activated carbon, fine wood powder, sodium chloride and water in a weight ratio of about 5:16:3:2:6.

Immediately following its fabrication, heating component 20 was adhered onto the adhesive tape 18. The adhesive bottom of the heating component chamber secured the heating component 20 to the top of the adhesive tape. The integrated device was then immediately sealed into an air-tight pouch 6 made of a barrier film (Perfecseal 35785). Once the integrated CHADD patch was sealed in the pouch, the formulation 10, the heat generating medium 34 and the outside environment were completely separated from each other, so that no substantial exchange of substance could take place among them during storage.

In order to use the integrated patch, pouch 6 was cut open, and the integrated device was removed from the pouch. The adhesive tape 18 was peeled from tray 8 from one end. Since leading edge 17 (see FIG. 3) of the barrier film 16 on that end was not sealed onto tray 8 but was adhered to adhesive tape 18, the barrier film 16 came off the tray 8 with the adhesive tape 18 when adhesive tape 18 was peeled off tray 8. Since the gauze 12 was heat sealed onto barrier film 16 and the formulation was attached to gauze 12, when adhesive tape 18 was peeled off tray 8, both the drug formulation and the heating component 20 came up with adhesive tape 18. The integrated patch was then applied onto human skin, with adhesive tape 18 providing the means for affixation.

A unique advantage of this design is that it prevents transfer of substance among the formulation, the heat generating medium and the outside environment, and is still very easy to use. The user simply opens the pouch, peels the integrated patch off the tray, and applies it onto the skin.

Tray 8 and barrier film 16 should have barrier properties that prevent substance exchange between the heat generating medium and the drug formulation. The main requirement of film 16 and tray 8 is that they both have excellent barrier properties to the substances in the heat generating medium and the drug formulation. Many materials meeting this requirement also possess good barrier properties to oxygen. One example of suitable materials for the barrier film 16 is a multi-layer laminated film having a layer of aluminum or other metal. The tray 8 may be made of any material that has the described barrier properties, that does not absorb/adsorb the drug in the formulation significantly, that is reasonably rigid in order to protect the formulation, and that is preferably not very expensive. Examples of such materials include: polyethylene, polypropylene, polystyrene, polycarbonate, polyvinyl chloride, Barex, Aclar, aluminum, or aluminum coated with a layer of polymer.

Any drug that may benefit from enhanced transdermal delivery may benefit from this invention. These drugs include but are not limited to: fentanyl, sufentanil and other narcotic analgesics; flurbiprofen, naproxen, ibuprofen and other non-steroidal anti-inflammatory agents, dexmathesone and other steroids; cox 2 inhibitors; nicotine; testosterone and other hormones; anti-viral agents; and anti-emetic agents.

Many different formats of drug delivery systems may benefit from this invention. These formats include but are not limited to: (1) a reservoir system in which the drug formulation is held between a backing film (which can be the barrier film 16 in the design of this invention) and a membrane, which may be rate-limiting or non rate-limiting; examples of these systems are Duragesic transdermal fentanyl patches (with rate-limiting membrane) and Androderm transdermal testosterone patches (with non-rate-limiting membrane) (2) a matrix system in which the active drug is mixed in a matrix which may be an adhesive matrix (example: Nicotrol transdermal nicotine patches) or a non glue matrix.

An experiment was conducted to evaluate the effect of the integrated heating/local anesthetic patch. Eight integrated heating/local anesthetic patches similar to the integrated CHADD patch described above were placed on the arms of each of six volunteers. The patches were removed at predetermined time intervals, and the skin under the patches were scratched to determine the level of anesthesia immediately following the removal of the patches. The following sensation score system was used to gauge the level of anesthesia: 0=No sensation, 1=dull sensation, 2=sharp/scratching sensation. Table A shows the results.

TABLE A

| Time (min) | Volunteer #1 | Volunteer #2 | Volunteer #3 | Volunteer #4 | Volunteer #5 | Volunteer #6 |
|---|---|---|---|---|---|---|
| 5    | 2 | 2 | 2 | 2 | 2 | 2 |
| 10   | 1 | 2 | 2 | 2 | 2 | 1 |
| 12.5 | 1 | 0 | 2 | 1 | 2 | 0 |
| 15   | 0 | 0 | 1 | 1 | 0 | 0 |
| 17.5 | 0 | 0 | 1 | 2 | 2 | 0 |
| 20   | 0 | 0 | 0 | 2 | 0 | 0 |
| 22.5 | 0 | 0 | 0 | 1 | 0 | 0 |
| 25   | 0 | 0 | 0 | 0 | 0 | 0 |

The results in Table A suggest that the integrated patch is capable of numbing the skin rapidly.

EXAMPLE 2

In another embodiment of the present invention, the integrated patch 2 is comprised of drug delivery component 4 and temperature control component 20. Drug delivery component 4 comprises a tray 8 having a width of about 2.5 inches and a length of about 3.0 inches, the tray being composed of high density polyethylene (HDPE). Tray 8 has barrier properties which inhibit or prevent the substance transfer between drug formulation 10 disposed within tray 8 and between the drug formulation and the environment on the other side of tray 8. Tray 8 defines a formulation reservoir 40 having a width of about 1 inch and a length of about 1.65 inches.

Drug formulation 10 is disposed within drug formulation reservoir 40 and is comprised of a lidocaine base, tetracaine base, polyvinylalcohol, lecithin (Phospolipon 90G), water and sodium borate.

Gauze 12 is laid over the drug formulation and is placed in contact with the drug formulation. The gauze layer is coated with a cross-linking agent which upon contact causes the liquid drug formulation in the tray to become a solid gel. Gauze 12 may be a gauze manufactured by Kendall. The gauze has a length of about 1.70 inches and a width of about 1.08 inches.

Prior to contact with the drug formulation the gauze is secured to a film barrier 16 with adhesive 14. Barrier film 16 is a heat sealable film having a width of about 1.5 inches and a length of about 2.25 inches. The film has barrier properties which inhibit the passing of oxygen and moisture. Perfecseal PerfecFelex™ 35786 medical packaging film is a suitable barrier film 16. The oxygen transmission rate is less than 0.01 cc/100 sq in/24 hrs. The moisture vapor transmission rate is less than 0.01 gm $H_2O$/100 sq in/24 hrs. The medical packaging film with the attached Kendall Gauze 12 covers the top of drug formulation 10. The barrier film 16 is heat sealed to the tray to prevent the loss of moisture from the drug formulation 10.

Adhesive layer 18 covers the heat sealable film 16. The adhesive tape dimensions are about 2.25 inches in width and about 2.75 inches in length. The piece of side of the adhesive tape faces downward attaching the barrier film to the adhesive tape and providing adhesive for attaching integrated patch 2 to the skin 50 of the user. 3M Transpore tape M1527-2 is a suitable adhesive tape 18.

Temperature control component 20 comprises a foam tape cover 28, a microporous membrane 60, a heat generating medium 34, a foam tape frame 24 and a bottom adhesive tape layer 22. Foam tape 24, cover 28 and taper layer 22 define a patch reservoir 52. The heat generating medium 34 is disposed within the patch reservoir 52. Heat generating medium 34 is composed of activated carbon, iron powder, a porous filler such as pinewood flour (less than 20 mesh), sodium chloride powder, and water (triple filtered). The temperature control component 20 has dimensions of about 1.5 inches in width by about 2.125 inches in length. The temperature control component may be a CHADD™ heating pad manufactured by ZARS, Inc., Salt Lake City, Utah. Temperature control component 20 is affixed to the adhesive tape layer of drug delivery component 4. The adhesive tape layer 18 also provides the means for securing integrated patch 2 to the skin surface. Integrated patch 2 is packaged in an air tight foil pouch 6. The pouch is about 3.0 inches in width by 5.5 inches in length. Pouch 6 may be formed of Perfecseal PerfecFlex™ 35785 medical packaging film. The pouch has barrier properties which prevent oxygen from entering the pouch. The oxygen transmission rate is less than 0.01 cc/100 sq in/24 hrs. It also has barrier properties to prevent moisture exchange between drug formulation, heating component and outside environment.

Alternatively, in place of a pouch, a tray constructed of materials with air and water impermeable properties may be used to isolate the drug formulation (for example a tray made of Teflon or aluminum coated with a polymer). A second barrier film may be attached to the tray over the heating pad to isolate the heating patch. The degree of isolation of the drug formulation and heating patch will depend upon the specific heating patch and drug formulation used.

EXAMPLE 3

In actual experimentation a temperature control component 100 was a Controlled Heat-Aided Drug Delivery (CHADD) patch comprising side walls 106 defined by a ⅛ inch thick rectangular foam tape (2 layer of No. 1779 1/16" white foam tape, 3M CORPORATION, MINNEAPOLIS, MINN., USA Corporation, Minneapolis, Minn., USA) with an outer dimension of about 2.25 inches by 4 inches with an opening therein having an inner dimension of about 1.76 inches by 3.5 inches, the bottom wall 102 comprising rectangular medical tape (No. 1525L plastic medical tape, 3M Corporation, Minneapolis, Minn., USA Corporation), of a dimension of about 2.25 inches by 4 inches with a non-adhesive side attached to the bottom of the side walls 106, with optional spacers 112 (not employed) and a top wall 104 comprising a rectangular 1/32 inch thick foam tape (No. 9773 1/32" tan foam tape, 3M Corporation, Minneapolis, Minn., USA Corporation), with forty-five holes 114 (diameters approximately 0.9 mm, in a 5 by 9 pattern with about 7.5 mm to 8.0 mm center spacing) there through. The side walls 106, the bottom wall 102, and the top wall 104, define a chamber. The holes 114 of the top wall 104 are covered by an air permeable membrane 116 comprising a microporous membrane (No. 9711 microporous polyethylene film—CoTram™, 3M Corporation, Minneapolis, Minn., USA Corporation), disposed between the top wall 104 and the temperature regulating mechanism 108. The side walls 106, the bottom wall 102, and the top wall 104, all have ⅛" rounded corners. The temperature regulating mechanism 108 disposed in the chamber comprised a mixture of activated carbon (HDC grade—Novit Americas, Inc., USA), iron powder (grade R1430—ISP Technologies, USA), saw dust (Wood Flour, Pine—Pioneer Sawdust, USA), sodium chloride and water in the weight ratio of approximately 5:15:3:2:6 weighing approximately 16.5 grams. The heat-generating medium composed of activated carbon, iron powder, sawdust, sodium chloride powder, and water was placed in the foam tape reservoir in the CHADD patch. The CHADD patch was then placed into a heat sealable medical grade foil pouch and immediately sealed with a thermal impulse sealer. The temperature control component 100 is thereby sealed in an air-tight container immediately after fabrication.

The temperature control component 100 was tested on a volunteer with a temperature probe placed between the temperature control component 100 and the volunteer's skin to measure the temperature. The results of this temperature experiment are illustrated in Table B, which shows that the temperature control component 100 is capable of keeping the skin temperature to a narrow, elevated range of about 41° C. to 43° C. for extended periods of time (at least about 240 minutes).

TABLE B

| Time (minutes) | Temperature (° C.) |
|---|---|
| 0 | 30.6 |
| 1 | 31.8 |
| 2 | 33.6 |
| 3 | 35.2 |
| 4 | 36.6 |
| 5 | 38.0 |
| 6 | 39.1 |
| 7 | 39.9 |
| 8 | 40.5 |
| 9 | 41.1 |
| 10 | 41.5 |
| 11 | 41.9 |
| 12 | 42.3 |
| 13 | 42.5 |
| 14 | 42.5 |
| 15 | 42.5 |
| 16 | 42.5 |
| 17 | 42.5 |
| 18 | 42.5 |
| 19 | 42.5 |
| 20 | 42.5 |
| 22 | 42.4 |
| 24 | 42.4 |
| 26 | 42.3 |
| 28 | 42.2 |
| 30 | 42.5 |
| 35 | 42.5 |
| 40 | 42.6 |
| 45 | 42.6 |
| 60 | 42.5 |
| 75 | 42.8 |
| 90 | 42.7 |
| 120 | 42.6 |
| 150 | 42.3 |
| 180 | 42.0 |
| 210 | 41.8 |
| 240 | 41.0 |
| 255 | 40.4 |

EXAMPLE 4

In yet another experiment, the temperature control component 100 comprised side walls 106 defined by a 3/16 inch thick rectangular foam tape (3 layers of No. 1779 1/16" white foam tape, 3M Corporation, Minneapolis, Minn., USA Corporation), with an outer dimension of about 2.25 inches by 4 inches with an opening therein inner dimension of about 1.75 by 3.5 inches, the bottom wall 102 comprising rectangular medical tape (No. 1525L plastic medical tape, 3M Corporation, Minneapolis, Minn., USA Corporation), of a dimension of about 2.25 inches by 4 inches with a non-adhesive side attached to the bottom of the side walls 106, and a top wall 104 comprising a rectangular 1/32 inch thick foam tape (No. 9773 1/32" tan foam tape, 3M Corporation, Minneapolis, Minn., USA Corporation), with seventy-eight holes 114 there through (diameters approximately 1/32 inch, in a 6 by 13 pattern with about a 6 mm center spacing). The side walls 106, the bottom wall 102, and the top wall 104 define a chamber. The holes 114 of the top wall 104 are covered by an air permeable membrane 116 comprising a microporous membrane (no. 9711 CoTram™ membrane, 3M Corporation, Minneapolis, Minn., USA Corporation), disposed between the top wall 104 and the temperature regulating mechanism 108. The temperature regulating mechanism 108 disposed in the chamber comprised a mixture of activated carbon, iron powder, saw dust, sodium chloride and water in the weight ratio of approximately 5:15:3:2:6 weighing approximately 25 grams. This temperature control component 100 was tested on a volunteer's stomach with a temperature probe placed between the temperature control component 100 and the volunteer's skin to measure the temperature. The results of this temperature experiment are illustrated in Table C, which shows that the temperature control component 100 is capable of keeping the skin temperature to a narrow, elevated range between about 41 and 44° C. for extended periods of time (at least 450 minutes).

TABLE C

| Time (minutes) | Temperature (° C.) |
|---|---|
| 0 | 29.6 |
| 1 | 31.9 |
| 15 | 39.3 |
| 16 | 39.3 |
| 17 | 40.6 |
| 18 | 41.0 |
| 19 | 41.4 |
| 20 | 41.9 |
| 22 | 42.7 |
| 24 | 43.2 |
| 26 | 43.6 |
| 28 | 43.7 |
| 30 | 43.5 |
| 35 | 43.5 |
| 40 | 43.3 |
| 45 | 43.3 |
| 60 | 43.1 |
| 75 | 42.9 |

TABLE C-continued

| Time (minutes) | Temperature (° C.) |
|---|---|
| 90 | 43.0 |
| 120 | 43.0 |
| 150 | 43.2 |
| 180 | 43.0 |
| 210 | 42.6 |
| 240 | 42.5 |
| 270 | 42.3 |
| 270 | 42.3 |
| 300 | 43.0 |
| 330 | 43.0 |
| 360 | 42.6 |
| 390 | 42.6 |
| 420 | 42.5 |
| 450 | 41.9 |

EXAMPLE 5

Another example of the apparatus comprises administering an integrated patch capable of delivering a therapeutic agent and delivering controlled heat to the skin of the patient thereby reducing the onset time of the therapeutic agent. For example, an integrated patch having a layer of local anesthetic formulation on the applicator could be stored in an air tight and water vapor tight container. The integrated patch is removed from its container and placed upon the skin of the patient. The drug formulation contains the following ingredients:

1:1 eutectic mixture of lidocaine and tetracaine bases: 12% polyvinyl alcohol: 12% lecithin: 3% chloric acid, sodium salt: 1% water: 72%

The heat from the integrated patch increases the temperature of the contact surface of the skin to a narrow temperature range between about 38° C. and 45° C., preferably about 39° C. and 44° C., and maintains this temperature for a period of time (i.e., approximately 30 minutes). During this time the heat increases the speed of the analgesic release from the integrated patch, the permeation rate across the skin. The shortened onset time can dramatically improve the ability of the therapeutic agent to meet the needs of a patient.

EXAMPLE 6

An example of using the inventive apparatus comprises administering an integrated patch capable of delivering the testosterone agent and delivering controlled heat to the skin of the patient thereby mimicking natural circadian patterns of testosterone in the blood stream. The user places the integrated patch on first thing in the morning (i.e. 7:00 am). The integrated patch lasts for 3–4 hours before the oxidation reaction which provides the heat for the heating element is complete, and no further heat is generated. Thus the testosterone concentration in the user's blood stream peaks around 10:00 or 11:00 a.m. The user continues to wear the patch after the heat generating element has died, and removes the patch before retiring to bed in the evening. Thus the user receives a concentration of testosterone in his blood stream that mimics the natural circadian pattern for the day.

EXAMPLE 7

An example of using the inventive apparatus comprises administering an integrated patch capable of delivering a therapeutic agent and delivering controlled heat to the skin of a patient thereby affording more effective temperature control. Certain drugs have relatively low therapeutic indices, meaning that the differences between the therapeutic dose and the dose which can cause serious reactions and undesired side effects are small. Thus, dermal delivery of such drugs can be dangerous (overdose) or ineffective (underdose). A number of temperature related factors can affect the delivery rate of a drug from a dermal drug delivery system, such as highly variable ambient temperatures, and skin temperatures. A dermal drug delivery system which has a fully integrated temperature control component will be more effective at controlling the temperature of the delivery system within a prescribed range. An integrated temperature control component will be less subject to unaccounted for variations in the drug delivery system. Such variations could prevent a dermal drug delivery system having an entirely separate temperature control mechanism from maintaining the prescribed temperature range during drug delivery. Examples of drugs and classes of drugs that may benefit from this feature of an integrated patch may include nicotine, nitroglycerin, clonidine, fentanyl, sufentanil, and insulin; and classes of drugs such as non-steroidal anti-inflammatory agents, anti-hypertensive agents, analgesic agents, anti-diabetic agents, anti-migraine agents and $COX_2$ inhibitors.

EXAMPLE 8

Another example of using the inventive apparatus comprises administering an integrated patch capable of delivering a therapeutic agent and delivering controlled heat to the skin of a patient thereby driving the therapeutic agent deeper into the skin and toward a target site. For example, if a person injures a joint such as an elbow or knee the user can apply an integrated patch containing an analgesic formula with a therapeutic agent such as dexamethasone, winter cream oil, or the like non-steroidal anti-inflammatory agents. The heat generated by the temperature control component will drive the therapeutic agent toward the target site and the increased blood flow in use by the heat takes the therapeutic agent deeper into the joint.

EXAMPLE 9

Another example of using the inventive apparatus comprises administering an integrated patch capable of delivering a therapeutic agent and delivering controlled heat to the skin of a patient thereby increasing the diffusion coefficient of the active ingredients in the formulation and/or increasing the permeability coefficient across a rate limiting membrane increasing the circulation of blood and other body fluid in the tissues (including the skin) under and around the integrated patch.

By way of example, if the use of a particular drug formulation is made impractical by its having a diffusion coefficient or permeability coefficient that is low whereby the inability of the tissues to distribute the absorbed formulation effectively, use of the formulation in an integrated patch may prove practical.

The increased temperature provided by the temperature control component in the integrated patch may increase the diffusion coefficient of the active ingredient in the formulation and increase the permeability coefficient across the rate limiting membrane as well as increasing circulation of blood and body fluids in the tissues proximate to the application site of the integrated patch.

Although Examples 1–8 discuss the application of specific drugs, it is, of course, understood that the present invention is not limited to any particular drug(s). It is understood that a considerable variety of drug classes and specific drugs may be used with the present invention. The drug classes can include without limitation androgen, estrogen, non-steroidal anti inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, and anti-obesity agents. Specific drugs can include without limitation nicotine, testosterone, estradoil, nitroglycerin, clonidine, dexamethasone, wintergreen oil, tetracaine, lidocaine, fentanyl, sufentanil, progestrone, insulin, Vitamin A, Vitamin C, Vitamin E, prilocaine, bupivacaine, sumatriptan, dihydroergotamine, and $COX_2$ inhibitors.

EXAMPLE 10

In another example an integrated patch 2 contains no drug formulation 10. In the event that particulate elements of a drug formulation such as a therapeutic agent or permeation enhancer, cannot practically be stored with an integrated patch, an embodiment of the present invention employs an integrated patch with such a drug formulation.

A patient or caregiver opens the storage container (not shown) of the integrated patch thus activating the temperature control component. A drug that is unstable in the ideal transdermal formulation is mixed with the rest of the ingredients of said ideal transdermal formulation, shortly before use (i.e. a drug unstable in aqueous matrixes, so it is stored freeze-dried powder or flakes. It us mixed with a mixture that has all the ingredients except the active drug to form a transdermal formulation shortly before use). The formulation can then be loaded into the integrated patch in the example before on application on skin.

The integrated patch is then placed on the patient's skin where the temperature control component heats the drug formulation and the patient's skin to within a narrow range of temperatures between 38° and 45° C., preferably between about 39° C. and 44° C., most preferably between 40° C. and 43° C., and maintains this temperature for a period of time. The user may then remove the patch when the treatment is finished.

EXAMPLE 11

In some instances it may be beneficial to include a rate limiting membrane as part of the drug applicator component. An integrated CHADD patch similar to that described in Example 1 is contemplated except that in the present example, the drug formulation is enclosed is the space defined by barrier film 16 on the top and a rate limiting membrane on the bottom. Rate limiting membrane is slightly smaller than the barrier film 16 and is sealed on to the barrier film 16 along the edges of membrane to form an enclosed space formulation reservoir. The barrier film 16 is then sealed to tray 8 completely enclosing the drug formulation in a maimer similar to that described in Example 1. The adhesive tape can be secured to the barrier film as explained in Example 1. The integrated CHADD patch with a rate limiting membrane is then enclosed in an air-tight pouch for storage until use.

To use the integrated CHADD patch with the rate limiting membrane, the user opens the air-tight package, peels the integrated CHADD patch off of the tray 8 by pulling up the adhesive tape. As discussed in Example 1, heating component 20 and the drug applicator and formulation will come up with the adhesive tape. The integrated patch is then applied to human skin with the rate limiting membrane disposed between the drug formulation and the skin.

In the example above, a layer of adhesive or formulation may be disposed on the rate limiting membrane, outside of the formulation reservoir. This layer of adhesive or formulation may contain the active drug. This layer of adhesive is also sealed in the space between film 16 and tray 8, and is between the rate limiting membrane and the skin when the integrated patch is applied to the skin.

EXAMPLE 12

An integrated CHADD patch may benefit from the addition of a non rate-limiting membrane disposed within the drug delivery component, similar to the rate limiting membrane described in Example 11. Such a membrane may be used to secure and hold the drug formulation in the reservoir defined by the membrane and the barrier film.

EXAMPLE 13

An integrated CHADD patch similar to that in Example 12, except that the active drug in the delivery component is fentanyl, sufentanil or carfentanil.

EXAMPLE 14

An integrated CHADD patch similar to that in Example 11, except that the active drug in the drug delivery component is any drug for which overdose is dangerous to the user such as a narcotic, such that a rate limiting membrane is desired.

EXAMPLE 15

An integrated CHADD patch similar to that in Example 12, except that the active drug in the drug delivery component testosterone.

EXAMPLE 16

An integrated CHADD patch similar to that in Example 12, except that the active drug in the delivery component is a non-steroidal, anti-inflammatory drug.

EXAMPLE 17

An integrated CHADD patch similar to that in Example 12, except that the active drug in the drug delivery component is selected from the group of dexmethasone, local anesthetics, and antihypertensive drugs.

EXAMPLE 18

An integrated CHADD patch similar to that in example 1, except that the drug delivery component contains steroid.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A dermal drug delivery system comprising:
    a temperature control component that is configured to selectively control an amount of heat generated by oxygen exposure;
    a drug delivery component coupled to the temperature control component; and means for preventing a transfer of substances between said temperature control component and said drug delivery component.

2. The dermal drug delivery system as set forth in claim 1, wherein the means for preventing a transfer of substances comprises a tray and a barrier film.

3. The dermal drug delivery system as set forth in claim 1, wherein the drug delivery component further comprises a tray defining a drug formulation reservoir and a drug formulation disposed within the drug formulation reservoir.

4. The dermal drug delivery system as set forth in claim 1, wherein the drug delivery component further comprises:
a tray;
a drug applicator; and
a drug formulation adherable to the drug applicator.

5. The dermal drug delivery system as set forth in claim 2, wherein the tray is substantially impermeable to moisture.

6. The dermal drug delivery system as set forth in claim 1, wherein the temperature control component comprises a heat generating element that is disposed within a chamber defined by a top wall, at least one side wall, and a bottom wall.

7. The dermal drug delivery system as set forth in claim 1, wherein the drug delivery component is selectively attachable to a patient's skin, and wherein the temperature control component heats the skin under the drug delivery system to a temperature range between about 38° and 45° C.

8. The dermal drug delivery system as set forth in claim 1, wherein the temperature control component comprises a chamber defined by a foam tape frame and a base.

9. The dermal drug delivery system as set forth in claim 1, wherein the temperature control component comprises a heat generating medium disposed within a patch reservoir.

10. The dermal drug delivery system as set forth in claim 9, wherein the heat generating medium comprises iron and activated carbon.

11. The dermal drug delivery system as set forth in claim 1, wherein the temperature control component comprises exposably covered holes.

12. A dermal drug delivery kit comprising:
a drug delivery component;
a heat generating element that is configured to generate an amount of heat upon exposure to oxygen; and
a temperature control component configured to selectively control the amount of heat.

13. The dermal drug delivery kit as set forth in claim 12, wherein the drug delivery component comprises a barrier to inhibit a transfer of one or more substances into or out of the drug delivery component.

14. The dermal drug delivery kit as set forth in claim 12, wherein the drug delivery component comprises a drug formulation applicator and a drug formulation.

15. The dermal drug delivery system as set forth in claim 4, wherein the drug applicator comprises:
a film barrier having a top side;
a layer of fabric material coupled to the film barrier; and
an adhesive tape layer having an adhesive bottom side, wherein the top side of the film barrier is adhered to the bottom adhesive side of the tape layer.

16. The dermal drug delivery kit as set forth in claim 15, wherein the temperature control component is activated upon opening the kit and exposing the temperature control component to air and wherein the drug delivery component is separated from the tray in preparation for application to the skin of a user, said separation completely removing both the drug delivery component and the temperature control component in a single motion.

17. A dermal drug delivery system comprising:
a temperature control component configured to selectively control an amount of heat generated by exposure to oxygen; and
a drug delivery component associated with the temperature control component.

18. The dermal drug delivery system as set forth in claim 17, wherein the oxygen is from ambient air.

19. The dermal drug delivery system as set forth in claim 17, further comprising means for preventing undesired heat loss.

20. The dermal drug delivery system as set forth in claim 17, wherein the heat is generated by a heat generating medium comprising activated carbon, iron, and water.

21. The dermal drug delivery system as set forth in claim 17, wherein the drug delivery component comprises a drug formulation in a substantially two-dimensional matrix.

22. The dermal drug delivery system as set forth in claim 17, wherein the drug delivery component comprises a drug formulation disposed between a backing film and a rate-limiting membrane.

23. The dermal drug delivery system as set forth in claim 17, wherein the drug delivery component comprises a drug formulation disposed between a backing film and a non rate-limiting membrane.

24. The dermal drug delivery system as set forth in claim 17, wherein the drug delivery component comprises a drug selected from the group of fentanyl, sufentanil, carfentanil, testosterone, lidocaine, tetracaine, prilocaine, lopivocaine, bupivacaine, procaine, flurbiprofen, naproxen, ibuprofen, and dexmathesone.

25. The dermal drug delivery system as set forth in claim 17, wherein the drug delivery component comprises at least one of:
(i) an analgesic;
(ii) an anti-inflammatory agent;
(iii) a steroid;
(iv) an androgen;
(v) an estrogen;
(vi) a hormone;
(vii) an anti-viral agent;
(viii) an anti-asthma agent;
(ix) a cardiovascular agent;
(x) an anti-hypertension agent;
(xi) an antidepressant; and
(xii) a cox2 inhibitor.

26. The dermal drug delivery system as set forth in claim 17, further comprising means to isolate the drug delivery component from the environment.

27. The dermal drug delivery system as set forth in claim 17, further comprising means to prevent a transfer of one or more substances between said heating component and said drug delivery component.

28. The dermal drug delivery system as set forth in claim 27, wherein the means to prevent a transfer of one or more substances between said heating component and said drug delivery component comprises at least one of:
(i) a barrier material placed between said heating component and said drug delivery component;
(ii) said drug delivery component sealed into a space completely enveloped by a material substantially impermeable to moisture or alcohol; and
(iii) said heating component sealed into a space completely enveloped by a material substantially impermeable to moisture or alcohol.

29. A method for preparing a dermal drug delivery system that selectively employs heat generated by oxygen exposure, the method comprising the steps for:

disposing an anesthetic formulation within a formulation reservoir of a tray;

securing the anesthetic formulation within the tray to a drug applicator;

isolating from both an outside environment and a temperature control component the anesthetic formulation within the tray;

securing the temperature control component to the drug applicator, wherein the temperature control component selectively controls the heat generated by oxygen exposure; and isolating the temperature control component from both the outside environment and from the anesthetic formulation.

30. The method of claim 29, wherein the step for securing the drug formulation comprises the steps for:

impregnating a layer of fabric material with a boric acid, sodium salt; and placing said fabric material in contact with said formulation, said formulation containing polyvinyl alcohol, to cause the drug formulation to solidify as a gel onto the fabric material.

31. The method of claim 30, wherein the step for isolating the drug formulation comprises the step for placing a heat sealable barrier film on top of the fabric material and sealing said barrier film to the tray and the fabric material.

32. The method of claim 31, wherein a portion of the barrier film is not sealed onto the tray in order to provide a leading edge for peeling.

33. The method of claim 29, wherein the temperature control component is a CHADD patch.

34. An integrated temperature control and dermal drug delivery system comprising:

an isolated temperature control component that selectively controls heat generated from oxygen exposure; and an isolated drug formulation integrated with the isolated temperature control component.

35. The system of claim 34, further comprising a means for affixing the system to human skin.

36. The method of claim 29, further comprising peeling both the drug formulation and temperature control component from the tray in a single action.

37. A method for fabricating a dermal drug delivery system having a selectively controllable heating component that generates heat upon exposure to oxygen, the method comprising the steps for:

providing a selectively controllable heating component configured to generate heat when exposed to oxygen;

providing a drug delivery component comprising a formulation that includes at least one pharmaceutically active substance;

coupling said heating component with said drug delivery component; and sealing either said heating component or said drug delivery component into a space completely enveloped by one or more materials that are substantially impermeable to moisture or alcohol.

* * * * *